United States Patent
Fröjd et al.

(10) Patent No.: US 8,042,689 B2
(45) Date of Patent: Oct. 25, 2011

(54) EXTRAVASCULAR SYSTEM PACKAGING SYSTEMS

(75) Inventors: Patric Fröjd, Malmö (SE); Per Axel Torell, Växjö (SE); Kristoffer Glowacki, Staffanstorp (SE); Måns Wemmert, Ängelholm (SE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 684 days.

(21) Appl. No.: 11/943,342

(22) Filed: Nov. 20, 2007

(65) Prior Publication Data

US 2008/0135443 A1 Jun. 12, 2008

Related U.S. Application Data

(60) Provisional application No. 60/867,045, filed on Nov. 22, 2006.

(51) Int. Cl.
*B65D 73/00* (2006.01)
(52) U.S. Cl. .......................... 206/464; 206/467; 206/471
(58) Field of Classification Search .................. 206/467, 206/468, 469, 470, 471, 461, 462, 463, 464, 206/465, 364, 365, 438, 439
See application file for complete search history.

(56) References Cited

U.S. PATENT DOCUMENTS

| | | | |
|---|---|---|---|
| 3,353,664 A | 11/1967 | Armentrout et al. | |
| 3,625,353 A | 12/1971 | Ishii | |
| 4,730,726 A * | 3/1988 | Holzwarth | 206/204 |
| 4,921,096 A | 5/1990 | McFarlane | |
| 5,082,112 A * | 1/1992 | Dunklee | 206/363 |
| 5,105,942 A | 4/1992 | van Veen et al. | |
| 5,133,454 A * | 7/1992 | Hammer | 206/364 |
| 5,176,258 A * | 1/1993 | Antal | 206/461 |
| 5,290,265 A | 3/1994 | Davis et al. | |
| 5,293,993 A * | 3/1994 | Yates et al. | 206/365 |
| 5,353,929 A * | 10/1994 | Foster | 206/364 |
| 5,379,895 A * | 1/1995 | Foslien | 206/363 |
| 5,407,070 A * | 4/1995 | Bascos et al. | 206/365 |
| 5,758,775 A | 6/1998 | Lowe | |
| 5,996,845 A * | 12/1999 | Chan | 222/107 |
| 6,026,959 A | 2/2000 | Lowe | |
| 6,170,666 B1 * | 1/2001 | DesLauriers | 206/756 |
| 6,357,589 B2 | 3/2002 | Schmidt et al. | |
| 6,915,901 B2 * | 7/2005 | Feinberg et al. | 206/363 |
| 6,994,213 B2 | 2/2006 | Giard, Jr. et al. | |
| 2005/0098467 A1 * | 5/2005 | Agakanian | 206/471 |
| 2006/0009742 A1 | 1/2006 | Solazzo | |

* cited by examiner

*Primary Examiner* — Jacob K Ackun
(74) *Attorney, Agent, or Firm* — Mony R. Ghose; Kirton & McConkie (57) ABSTRACT

Extravascular system packaging systems are adapted to facilitate opening of the package and to facilitate one or more auxiliary uses of the packaging systems. Auxiliary uses include the use of at least a portion of the packaging system as a pre-insertion table and as a temporary disposal receptacle. In its use as a pre-insertion table, the packaging system is adapted to provide a stable temporary storage tool where the extravascular system is readily accessible to the medical practitioner. In its use as a temporary disposal receptacle, the packaging system is adapted to provide a stabilized receptacle adapted to temporarily receive a deployed needle assembly until the needle assembly can be properly disposed of in a sharps container.

10 Claims, 5 Drawing Sheets

Prior Art

EXTRAVASCULAR SYSTEM PACKAGING SYSTEMS

RELATED APPLICATIONS

This application claims the benefit of U.S. Provisional Application No. 60/867,045, filed Nov. 22, 2006, entitled VASCULAR ACCESS DEVICE PACKAGING SYSTEMS, which is incorporated herein by reference.

BACKGROUND

This disclosure relates generally to extravascular systems, including packaging assemblies and devices used with catheter assemblies. Generally, extravascular systems are used for communicating fluid with the vascular system of patients. For example, catheters are used for infusing fluid, such as normal saline solution, various medicaments, and total parenteral nutrition, into a patient, withdrawing blood from a patient, or monitoring various parameters of the patient's vascular system.

A common type of intravenous (IV) catheter is an over-the-needle peripheral IV catheter. As its name implies, an over-the-needle catheter is mounted over an introducer needle having a sharp distal tip. At least the inner surface of the distal portion of the catheter tightly engages the outer surface of the needle to prevent peelback of the catheter and thus facilitate insertion of the catheter into the blood vessel. The catheter and the introducer needle are assembled so that the distal tip of the introducer needle extends beyond the distal tip of the catheter with the bevel of the needle facing up away from the patient's skin. The catheter and introducer needle are generally inserted at a shallow angle through the patient's skin into a blood vessel.

In order to verify proper placement of the needle and/or catheter in the blood vessel, the clinician generally confirms that there is "flashback" of blood in a flashback chamber of the catheter assembly. Once proper placement of the catheter into the blood vessel is confirmed, the clinician may apply pressure to the blood vessel by pressing down on the patient's skin over the blood vessel distal of the introducer needle and the catheter. This finger pressure occludes the vessel, minimizing further blood flow through the introducer needle and the catheter.

The clinician may then withdraw the introducer needle from the catheter. The introducer needle may be withdrawn into a needle tip shield device that covers the needle tip and prevents accidental needle sticks. In general, a needle shield includes a housing and a sleeve or other similar device that is designed such that when the needle is withdrawn from the patient the needle tip will be trapped/captured within the needle tip shield. The purpose of these needle tip shield devices is to house the tip of the needle in a secure location, thereby avoiding the possibility of needle sticks after the needle and needle shield device are separated from the catheter, which is left in place to provide intravenous access to the patient.

As can be imagined, many extravascular systems are used by medical practitioners under conditions in which time is of the essence. Accordingly, the procedures in many utilizations of extravascular systems involve a first person, such as a nurse or technician, opening the sterile packaging in which the extravascular system is provided and making it available to the medical practitioner that will actually insert the extravascular system into the patient. The nurse that is opening the packaging of the extravascular system may be hurriedly opening several different packages and preparing several diverse instruments for use by the doctor, surgeon, or other practitioner. The opened packaging then is used often as a temporary housing or storage structure until the practitioner is ready to use the extravascular system. Additionally, once the practitioner has completed the insertion of the extravascular system, has withdrawn the needle, and separated the needle and needle shield device from the catheter, the practitioner and supporting personnel often place the shielded needle assembly back into the extravascular system packaging for temporary storage until one of the personnel has an opportunity to attend to its disposal.

BRIEF SUMMARY

The systems and methods of the present disclosure have been developed in response to problems and needs in the art that have not yet been fully resolved by currently available packaging systems for extravascular systems. Thus, these systems and methods are developed to provide more efficient packaging systems for extravascular systems capable of facilitating the preparation of the extravascular system for use and the temporary storage of the extravascular system after its use prior to proper disposal.

In one aspect of the present disclosure, the packaging systems include a base member including a pocket configured to receive an extravascular system. The packaging systems also include a cover member that is sealed at least around the edges of the pocket to contain the extravascular system and to promote sterility. The base member may include one or more flanges that extend away from the pocket to which the cover may be secured. The packaging systems are generally elongate packages having a distal end region and a proximal end region, corresponding to the distal and proximal ends of the extravascular system. The present packaging systems may also include at least one tear knob disposed in each of a distal end region and a proximal end region. The access points may be sized and positioned to facilitate the user's gripping of the cover member to tear the cover member away from the base member.

Additionally or alternatively, the packaging systems of the present disclosure may include a base member that is configured to accommodate the needle assembly, including a deployed needle cap, after it has been used to insert a catheter and has been separated from the catheter adapter. In such configurations, the temporary disposal receptacle is provided by a base member having a pocket configured with an enlarged segment toward the distal end region of the base member. The enlarged segment may be configured in various geometries and dimensions depending on the configuration of the deployed needle cap that is to be temporarily stored in the packaging assembly.

Additionally or alternatively, the packaging systems of the present disclosure may include a base member that is configured to accommodate the extravascular system, before and after use, and to provide a stabilized receptacle from which the extravascular system can be easily and safely retrieved even after the cover member has been removed or partially removed. The stabilized temporary receptacle may also be adapted to facilitate the safe and easy placement of a used needle assembly back into the receptacle after use.

BRIEF DESCRIPTION OF THE SEVERAL VIEWS OF THE DRAWINGS

In order that the manner in which the above-recited and other features and advantages of the present disclosure are obtained will be readily understood, a more particular description of the systems and methods briefly described above will be rendered by reference to specific embodiments thereof which are illustrated in the appended drawings. These drawings depict only typical embodiments of the systems and methods and are not therefore to be considered to limit the scope of the disclosure.

DETAILED DESCRIPTION OF THE INVENTION

The presently preferred embodiments of the present disclosure will be best understood by reference to the drawings. It will be readily understood that the components of the present disclosure, as generally described and illustrated in the figures herein, could be arranged and designed in a wide variety of different configurations. Thus, the following more detailed description, as represented in the figures, is not intended to limit the scope of the disclosure as claimed, but is merely representative of presently preferred embodiments of the disclosure Referring to FIG. 1, a perspective view illustrates an example of an extravascular system 10 prior to insertion. In this example the extravascular system 10 includes a catheter assembly 12, which is shown in its entirety. The catheter assembly 12 includes multiple component parts that will be described in greater detail in connection with FIG. 2.

Figure 2:
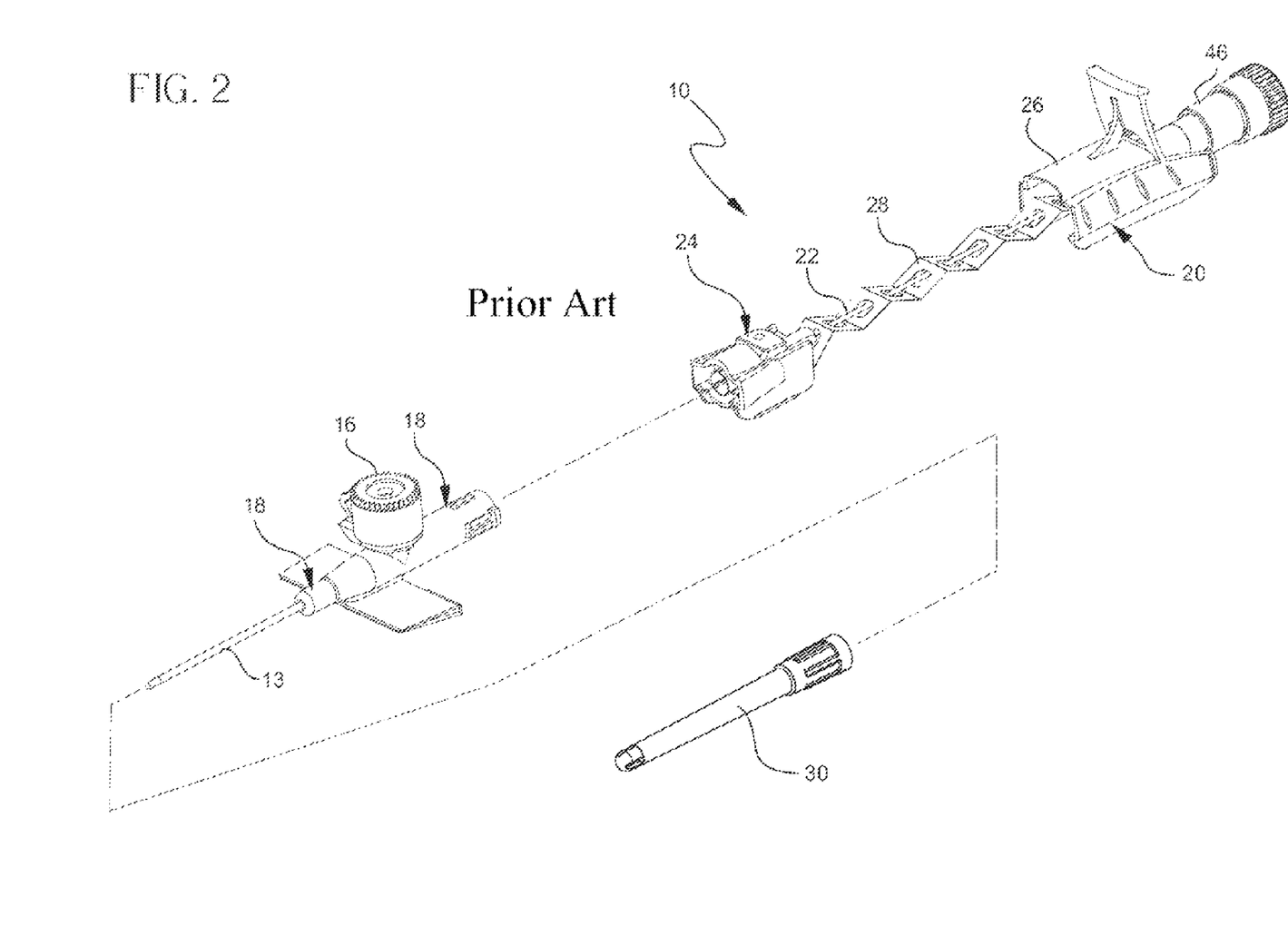
FIG. 2 is a perspective view of the extravascular system of FIG. 1 having the needle cap deployed.

Referring now to FIG. 2, a perspective view illustrates a deployed needle assembly 20 after it has been separated from other components of the catheter assembly 12. The catheter assembly 12 includes an extravascular system 10 such as a catheter 13, and cooperating elements. For example, the catheter assembly 12 may include a catheter adapter 18, which may be configured to cooperate with the needle assembly 20 during insertion of the catheter 13 and to provide other functions after the needle assembly 20 is removed. Additionally, the catheter assembly 12 may include a needle protection cap 30 positioned over the catheter 13 and the cannula 22 thereby protecting the sterility of the catheter 13 as well as protecting a user from an accidental stick by the cannula 22 prior to and following use of the extravascular system 10.

The exploded view of FIG. 2 further illustrates that the extravascular system 10 includes a needle assembly 20. The needle assembly 20 may include a variety of subcomponents, some examples of which are shown in FIG. 2. The needle assembly 20 may include a cannula 22 adapted to be inserted into the vascular system of a patient and to facilitate the insertion of the catheter 13 to the vascular system of a patient. Additionally, the needle assembly 20 may include a needle cap 24, a needle hub 26, and a tether 28 extending between the needle cap 24 and the needle hub 26.

Figure 1:
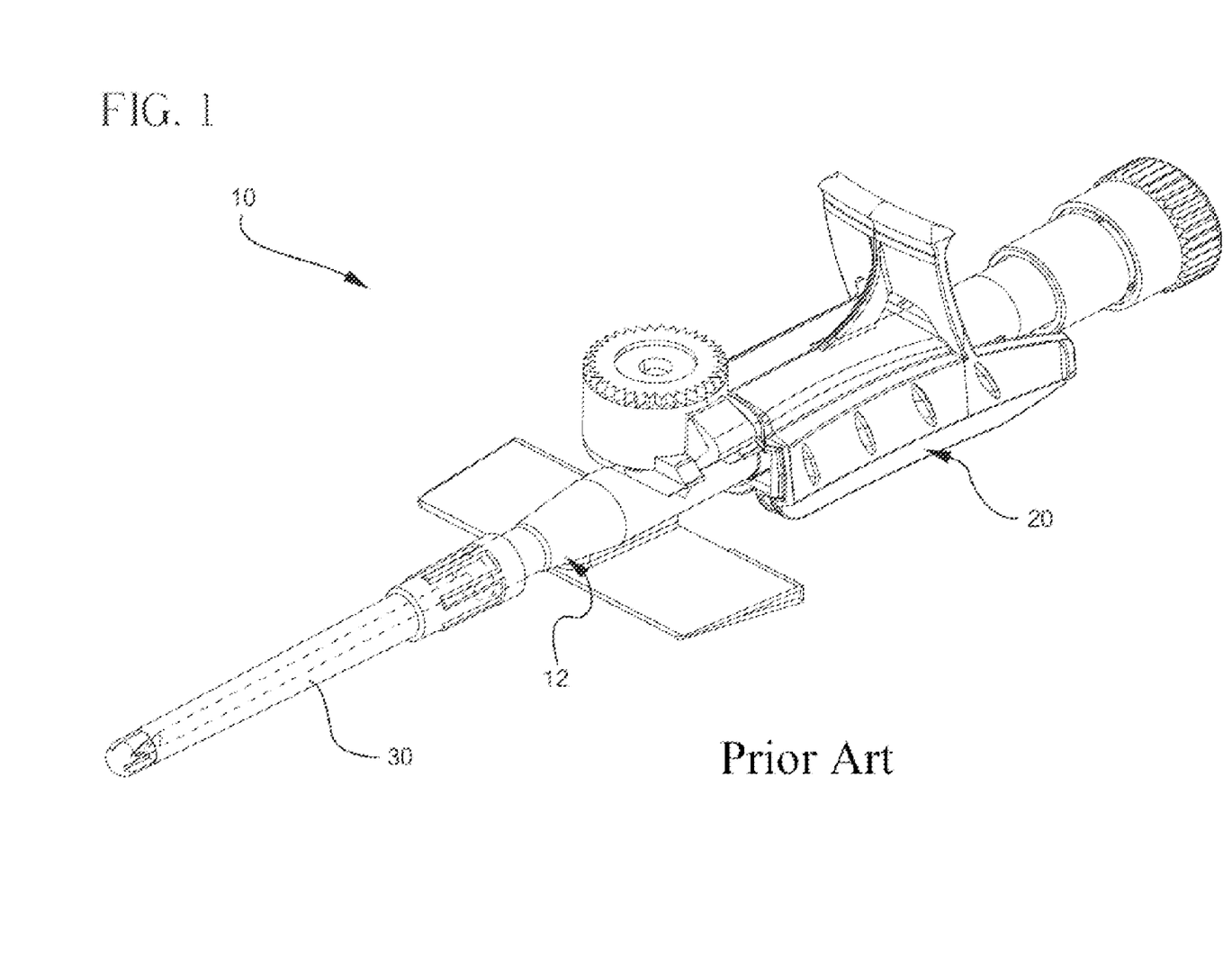
FIG. 1 includes a perspective view of an extravascular system in a pre-use configuration.

As can be seen by comparing FIGS. 1 and 2, the needle cap 24 and the tether 28 may be adapted to fit at least substantially inside the needle hub 26 when the needle assembly 20 is in the pre-use configuration. The needle assembly 20 may include additional parts or components adapted to provide the needle assembly 20 with the desired functionality. Similarly, the catheter assembly 12 may include additional or alternative parts and subcomponents depending on the configuration of the catheter assembly 12 and its intended usage. For example, the needle assembly 20 may include a protective plug 34 to preserve the sterility of the needle assembly prior to and following use of the extravascular system 10.

In further example, the needle hub 26 may be provided in a variety of configurations depending on the intended usage of the extravascular system 10 in which the needle assembly 20 is used. In one embodiment, the needle hub 26 may include features to improve the user's grip on the needle hub, to improve the user's ability to maneuver the needle assembly 20, and/or to provide other functionality to the needle hub 26 and/or the needle assembly 20 generally. In another embodiment, the needle cap 24 and the needle hub 26 may be adapted to allow at least a substantial portion of the needle cap 24 to be disposed within the needle hub 26 prior to deployment of the needle cap 24. Additionally, the needle cap 24 may be provided with elements adapted to selectively couple the needle cap 24 to the catheter adapter 18 such that when the needle assembly 20 is withdrawn from the catheter adapter 18 the needle cap 24 is separated from the needle hub 26 and drawn into the deployed position of FIG. 2. Additionally, the needle cap 24 may include lock-out mechanisms that control or limit the movement of the needle cap 24 relative to the cannula 22 once the needle cap 24 is disposed in the deployed condition.

The needle cap 24 may also include features adapted to improve the safety of the needle assembly 20 after its separation from a catheter adapter 18. In some uses of the extravascular system 10, some amount of the patient's blood may persist on the needle assembly 20, and particularly on the distal tip of the cannula 22, after the needle assembly 20 is separated from the catheter adapter 18. In some configurations of the needle cap 24, the needle cap 24 may include shields, reservoirs, caps, or other features adapted to minimize the possibility of spilling this blood and/or the possibility of users unintentionally contacting this blood. As evidenced by this list of variations and features that may be incorporated into the needle cap 24, numerous configurations of the needle cap 24 are within the scope of the present disclosure, some of which may include one or more of the features described herein.

Still referring to FIG. 2, the tether 28 of the needle assembly 20 is illustrated in its deployed condition coupling the needle cap 24 to the needle hub 26. The tether 28 is illustrated as being initially folded within the needle hub 26 and then unfolded and stretched along the cannula 22 as the needle cap 24 and tether 28 are deployed. While the tether 28 may include holes through each panel of the folded tether 28 to form a cannula passage, such a passage is not required. For example, the tether 28 may be adapted to be folded, or otherwise compacted, within the needle hub 26 without requiring passage of the cannula 22. Additionally or alternatively, other suitable relationships between the cannula 22 and the tether 28 may be implemented. The tether 28 may be made of conventional materials to provide the desired strength, sterility, and other properties. The tether 28 may be adapted to have a maximum deployed length that is selected to prevent the needle cap 24 from being separated from the needle assembly 20, such as being pulled from the distal end of the cannula 22.

Figure 3:
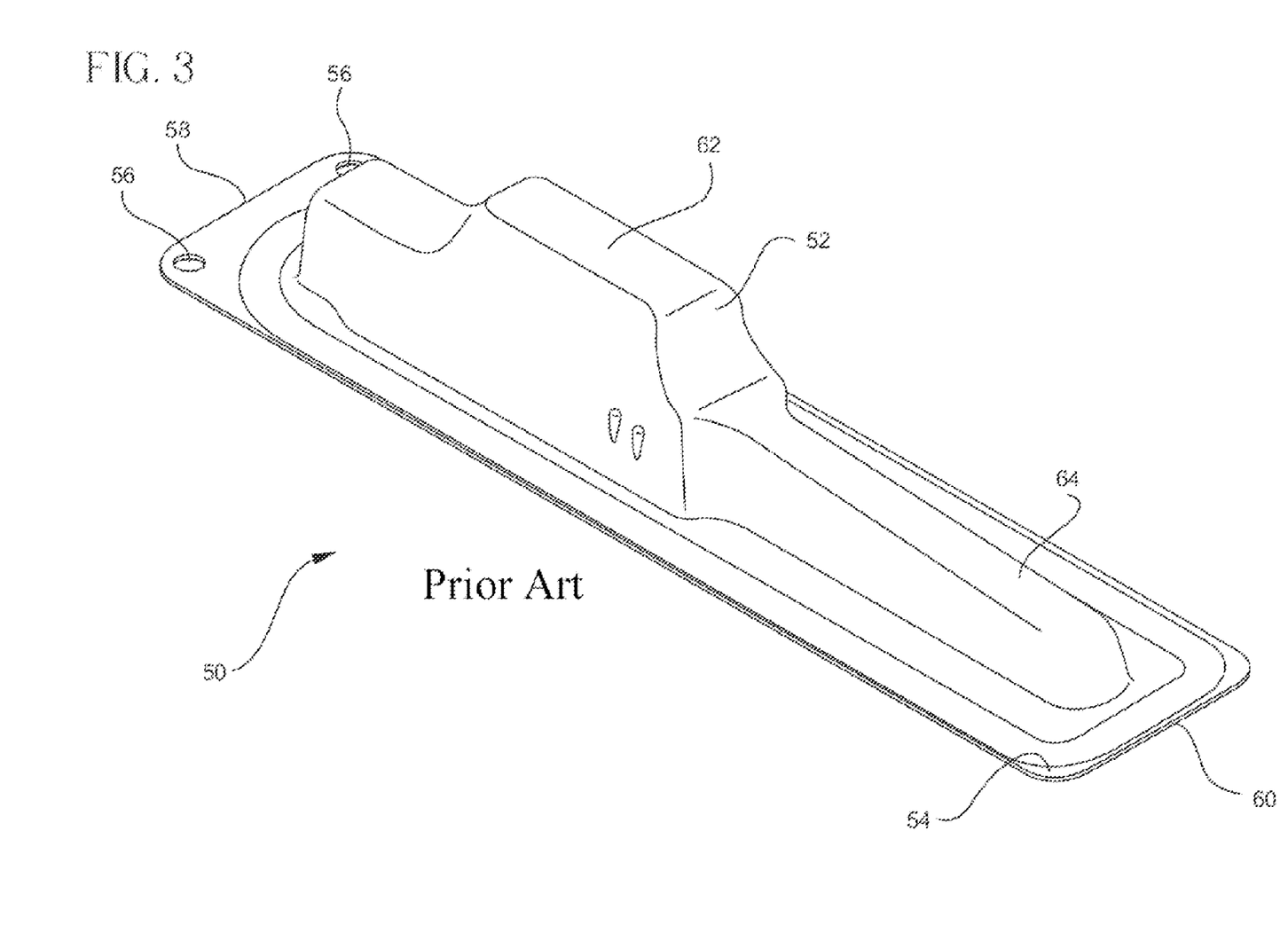
FIG. 3 is a perspective view of a conventional packaging assembly.

As introduced above, it has been reported that users of extravascular system 10 often utilize the packaging of the extravascular system 10 as a pre-insertion table prior to patient venipuncture and as a temporary disposal receptacle prior to properly discarding the needle assembly 20 into a sharps container. FIG. 3 illustrates a conventional packaging system 50 that has been used to package extravascular systems 10 such as those illustrated in FIGS. 1 and 2. The conventional packaging system 50 includes a blister package 52 and a cover member 54.

The blister package 52 is shown including access points, such as tear knobs 56, disposed at one end of the packaging system 50 and various contours to accommodate the extravascular system 10. For purposes of description, the conventional packaging system 50 will be referred to as including a proximal end region 58 and a distal end region 60 corresponding to the proximal and distal ends of the extravascular system 10. Accordingly, in FIG. 3, the access points 56 are provided at the proximal end region 58 of the packaging system 50. Conventional packaging systems 50 include only a single set of access points 56 disposed at one end of the package, which requires the user to find the correct end prior to opening the package. In the fast-paced environment in which many extravascular systems 10 are used, every added step slows down the medical practitioners.

Continuing with FIG. 3, the conventional packaging system 50 illustrates the conventional blister package 52 that is formed to fit around a extravascular system 10, such as those described above, as the assembly is provided from the manufacturer (i.e., prior to patient venipuncture). Accordingly, referring back to the illustration of FIG. 1, the blister package 52 is configured with a wide and deep pocket 62 toward the proximal end of the package system 50 and with a narrow and shallow pocket 64 toward the distal end of the package system 50. The blister package 52 includes other contours and dimensions adapted to receive and optionally secure the unused extravascular system 10 in the package.

While these conventional packaging systems 50 are suited for distribution and storage of the unused extravascular systems 10, they are ill-suited for the reported auxiliary uses of the packaging system 50. For example, consider the pre-insertion table usage where the packaging system 50 is opened by removing the cover member 54, inverting the blister package 52, and resting the blister package 52 on a table or other support adjacent to the patient. This usage is understood to be the result of nurses or other medical personnel preparing the instruments for convenient access by doctors or other medical personnel at the moment the instrument is needed.

With reference to FIG. 3, it can be seen that the blister package 52 in an inverted orientation would provide an inclined package having a pivot point provided by the narrow and shallow pocket 64. Accordingly, once the blister package 52 is inverted and rested on a table or other surface, the package system 50 often is not stable. For example, the opening to the package may be moved from a horizontally level position to a tilted position. Should the medical practitioner reach for the extravascular system 10 expecting it to be in a horizontally level position, the unexpected tilting of the package may slow the practitioner's actions. Additionally, the pivot point provided by the narrow, shallow pocket 64 may hinder the practitioner's actions in other ways. Moreover, in extreme situations, the pivot point may cause the package to tip and allow the extravascular system 10 to fall out of the packaging system 50. Depending on the circumstances, this may compromise the sterility of the device. For this reason, the use of the conventional packaging system 50 as a pre-insertion table is not considered good practice by device manufacturers. However, regardless of whether a practice is considered good by the manufacturer, medical practitioners often will do what is considered necessary, appropriate, or convenient under the circumstances. As will be seen in FIG. 4, the packaging systems of the present disclosure address the realities of the auxiliary uses of the product packaging.

Additionally, considering the exemplary auxiliary use of the product packaging as a temporary disposal receptacle for the needle assembly 20, the inverted blister package 52 of the conventional packaging system 50 is particularly poorly configured. With reference to FIGS. 1 and 2, the distal end of the extravascular system 10 in the pre-insertion configuration and the distal end of the needle assembly 20 after the catheter 13 has been inserted and the needle cap 24 deployed are dramatically different. The pre-insertion distal end of the extravascular system 10 is about the size of the cannula 22 and the distal end of the conventional blister package 52 is designed to accommodate the cannula 22 as shown in FIG. 1. However, once the needle cap 24 is deployed and positioned at the distal end of the cannula 22, the distal end of the needle assembly 20 is noticeably wider than the unprotected cannula 22. Accordingly, the needle assembly 20 with deployed needle cap 24 is not able to fit back into the blister package 52. The result is a needle assembly 20 that is not properly seated in an unstable blister package 52. When the blister package 52 is used as a temporary disposal receptacle, the instability provided by the narrow, shallow pocket 64 is a greater concern because the unseated needle assembly 20 creates a high center of gravity and is more likely to fall out of the packaging system 50. Fortunately, the sharp distal end of the needle assembly 20 is protected by the needle cap 24. However, the needle assembly 20 may still have blood or other fluids exposed. Accordingly, while prompt and immediately disposal into a sharps container is the best practice, if medical practitioners are going to use the packaging system 50 as a temporary disposal receptacle it is preferred to provide a receptacle into which the entire used needle assembly 20 can be placed.

Figure 4:
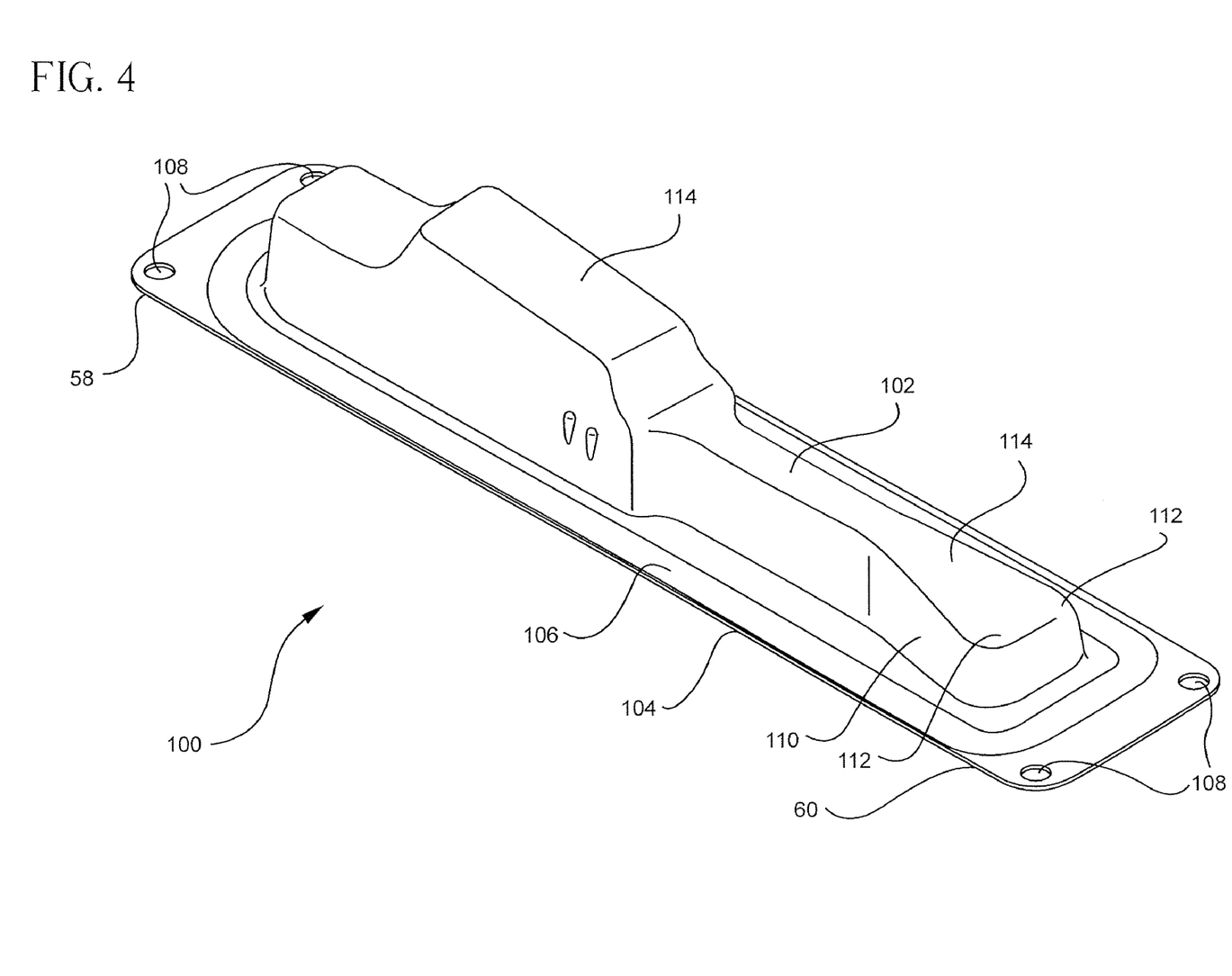
FIG. 4 is a perspective view of a packaging assembly according to the present disclosure.

Turning now to FIG. 4, an improved packaging system 100 according to the present disclosure is illustrated. The present packaging system 100 includes multiple features to address the various problems presented by the conventional packaging systems 50. Packaging systems incorporating any one or more of the features described herein are within the scope of the present disclosure. Accordingly, while each of the features may be combined into a single packaging system, the features are not required to be used together.

The present packaging system 100 includes a base member 102 and a cover member 104. The base member 102 may be thermo formed or molded, such as by injection molding. Suitable materials for the base member 102 include those materials used in conventional packaging systems to provide the blister package. The cover member 104 may include TYVEK® paper or other suitable material to cover the opening in the base member 102. The cover member 104 may be clear or semi-transparent and preferably may be sealed to the base member 102, such as with seal 106.

The present packaging system 100 also illustrates the use of multiple sets of access points 108, with one set disposed at each end of the packaging system 100. For ease of description, the present packaging system 100 will continue with the convention of referring to the opposing end regions as proximal end region 58 and distal end region 60. The access points 108 may be disposed at any suitable location within the end regions 58, 60 to facilitate the opening of the present packaging system 100. Similarly, any number of access points, such as tear knobs 108, may be used at each end of the packaging system 100. The present packaging systems 100 including access points 108 at both the proximal end region 58 and the distal end region 60 allows the user to open the packaging system 100 from either end, removing the requirement that the user find the proper end prior to opening the package. As indicated above, the efficiencies provided by this change may lead to great improvements for medical practitioners.

Additionally or alternatively, the packaging system 100 may include means other than access points for providing multiple access points to facilitate removal of the cover member 104. An important feature for any method of multiple access points is to position the access points at multiple locations on the packaging system 100. The final positioning of the access points should allow a technician or clinician to remove the cover member 104 from either end region 58, 60 with minimal need to reorient the packaging system 100.

For example, in one embodiment the packaging system 100 includes a cover member 104 comprising a surface area greater than the outer dimensions of the base member 102 opening. In this embodiment, the cover member 104 overlaps the opening of the base member 102 thereby providing a 360° flap-portion of the cover member 104 that may be secured by the technician to facilitate removal of the cover member 104. In another embodiment the cover member 104 may be modified to include tabs and/or extensions comprising the corners of the cover member such that when the cover member 104 is sealed to the base member 102, the tabs and/or extensions of the cover member 104 extend beyond the outer dimensions of the base member 102 opening thereby providing multiple access points to facilitate removal of the cover member 104.

In a final embodiment two or more corners of the base member 102 sealing surface are scored and/or clipped thereby creating a separation between the sealing surface corner pieces of the base member 102 and the remainder of the base member 102. In this same embodiment, the two or more scored and/or clipped corner pieces are attached to and positioned on the cover member 104 such that when the cover member 104 is attached to the sealing surface of the base member 102, the scored and/or clipped corner pieces are repositioned adjacent to the remainder of the base member 102. In this embodiment, each of the two or more repositioned corner pieces provide a tab-like access point to facilitate removal of the cover member 104.

Additionally or alternatively, packaging systems 100 according to the present disclosure may be provided with an enlarged pocket segment 110 toward the distal end region 60 of the base member 102. As illustrated, the enlarged pocket segment 110 has a dog-bone or somewhat triangular shape. The illustrated, packaging system 100 is merely illustrative and the enlarged pocket segment 110 may be provided in a variety of suitable configurations. In some implementations, the enlarged pocket segment 110 may be configured based on the dimensions and configuration of the needle cap 24 used in the extravascular system 10 for which the packaging system 100 is designed. Accordingly, the illustrated enlarged pocket segment 110 may be sized to accommodate the needle cap 24 illustrated in FIG. 2. The enlarged pocket segment 110, therefore, provides a suitable receptacle for the needle assembly 20 after the needle cap 24 has been deployed during withdrawal of the needle assembly 20 from the catheter assembly 12. Accordingly, the properly seated needle assembly 20 will be less likely to fall out of the packaging-turned-disposal-receptacle. Additionally, the properly seated needle assembly 20 will be less likely to expose practitioners to blood or other fluids that may be on the needle assembly 20. The enlarged pocket segment 110 may be configured to minimize packaging materials and to promote simplicity in manufacturing, such as by having optimized radii and curvatures. Additionally or alternatively, in some implementations, the enlarged pocket segment 110 or other portions of the base member 102 may be configured with retention tabs (not shown) to better retain the deployed needle assembly 20 in the temporary disposal receptacle after use.

The present packaging systems 100 may also include features adapted to improve the stability of the inverted base member 102 during its auxiliary uses as a pre-insertion table and/or as a temporary disposal receptacle. Exemplary adaptations may include feet extending to the sides of the pocket toward the distal end 60 of the base member 100. In configurations that do not include an enlarged pocket segment 110, the pocket toward the distal end 60 of the base member 100 may appear similar to the narrow, shallow pocket 64 of FIG. 3. However, to improve the stability of the base member 102 during auxiliary use, feet members (not shown) may extend to the sides of the pockets.

In more preferred configurations, the present packaging systems 100 may include both an enlarged pocket segment 110 and stabilizing structures. FIG. 4 illustrates such a preferred configuration. As illustrated, the enlarged pocket segment 110 includes wing portions 112 that extend laterally from the centerline of the packaging system 100. The wing portions 112, in addition to accommodating the width of the needle cap 24, may be adapted to provide stability to the inverted base member 102. The dimensions of the wing portions 112, therefore, may vary according to the dimensions of the packaging system 100 and the dimensions of the needle cap 24. The dog-bone configuration shown in FIG. 4 may be preferred in some implementations to provide the widest wing portion 112 possible to promote stability while still minimizing materials and facilitating manufacturing.

With continuing reference to FIG. 4, the present packaging system 100 may additionally or alternatively include one or more landing surfaces 114. The landing surfaces 114 may be disposed toward the distal end region 60 and/or the proximal end region 58. As illustrated, the landing surfaces 114 include wide surfaces to promote the stability of the inverted base member 102 when it is used in one or both of its auxiliary uses. Similar to the wing portions 112 described above, the width of the landing surfaces 114 reduces the wobbliness of the inverted base member 102. The width of the landing surfaces 114 may vary between packaging systems 100 and may be selected based at least in part on the dimensions of the needle assembly 20, both before and after use. For ease and economics of manufacture, the landing surfaces 114 may have a width that is just large enough to accommodate the extravascular system 10 before use and the deployed needle assembly 20 after use when such widths are sufficient to provide the desired degree of stability.

Additionally, the landing surfaces 114 may be adapted to maximize the contact area between the landing surfaces 114 and the surface upon which the inverted base member 102 is rested. As illustrated, the landing surfaces 114 are sloped to maximize the contact area. The angle of inclination of the landing surfaces 114 may be selected to provide a desired angle of presentation to the user and/or to provide a transition between the deeper pocket toward the proximal end region 58 and the more shallow pocket toward the distal end region 60. Depending on the configuration of the extravascular system 10 and the packaging system 100, the provision of landing surfaces 114 having enlarged contact areas may require adaptations of other aspects of the base member 102. For example, the shallow pocket toward the distal end region 60 may be deepened to reduce the elevational differences between to the two pocket regions. Similarly, the distal end of the deeper pocket may be made less deep than the proximal end of the deeper pocket, such as by increasing or decreasing the amount of space between the packaging materials and the extravascular system 10. The inclined surfaces of the landing surfaces 114 may be adapted to lower the center of gravity of the inverted base member 102, which will further increase the stability of the inverted base member 102.

The exemplary packaging system shown in FIG. 4 is representative of a packaging system 100 incorporating each of the features described above, including the landing surfaces 114, the enlarged pocket segment 110, the stabilizing wing segments 112, and the access points 108 disposed at both ends of the packaging system 100. Additionally, FIG. 4 illustrates one manner of incorporating each of these elements into a single packaging system while facilitating the manufacturing process and minimizing the packaging materials, such as by using fluid surfaces and curvatures without undercuts or other sharp turns in the material. While FIG. 4 illustrates a presently preferred configuration, the present disclosure encompasses other configurations that include one or more of the above described features. For example, the present disclosure encompasses packaging systems incorporating stabilizing members in the form of feet, flares, or flange member extending laterally from a shallow pocket at the distal end of the packaging system. Additionally, the present disclosure encompasses landing surfaces in the form of a raised platform extending away from the shallow pocket to be on the same level as the deeper pocket. Other variations on the structures and embodiments described herein are also within the scope of the present disclosure.

Figure 5:
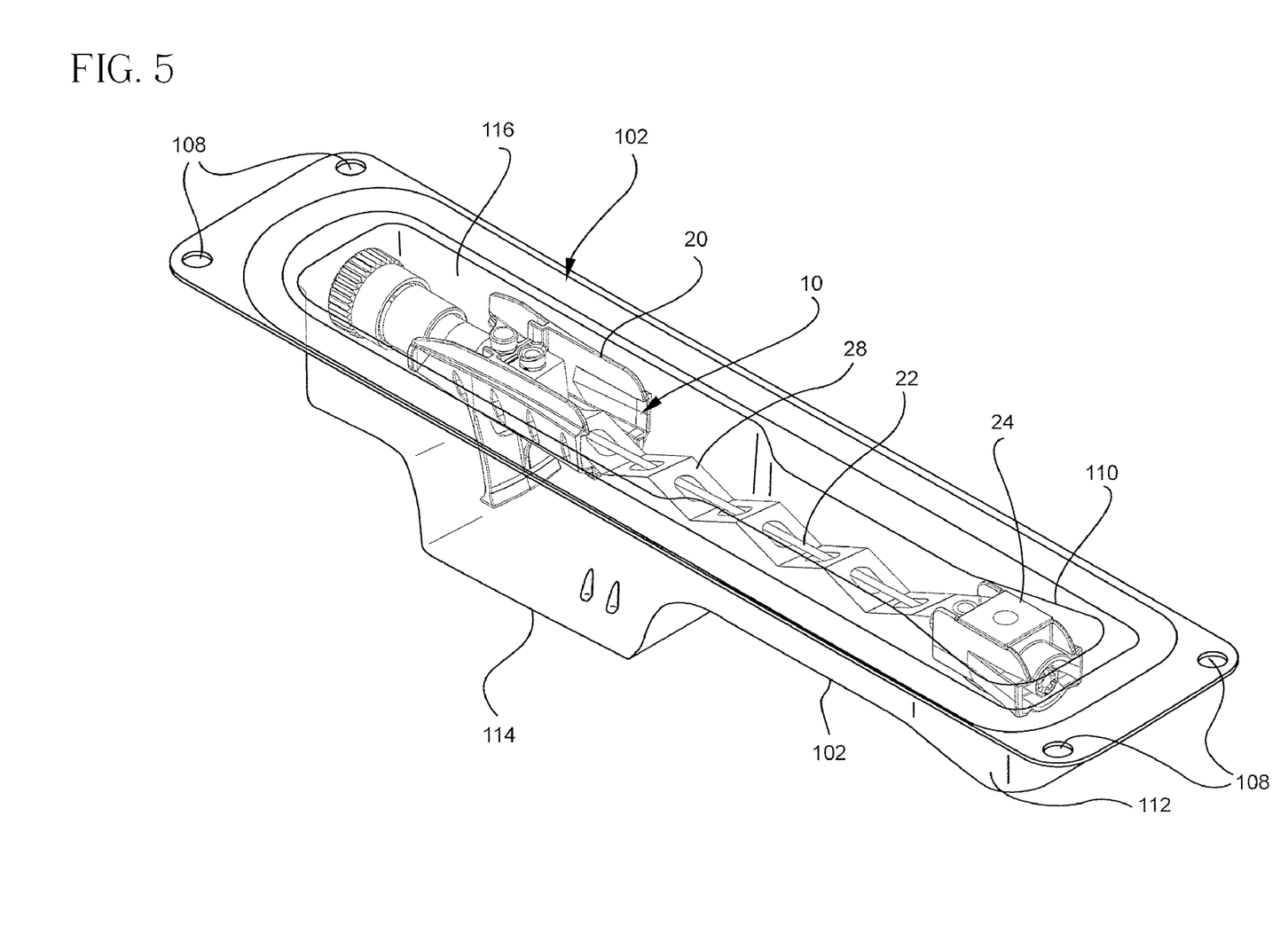
FIG. 5 is a perspective view of a packaging assembly in an inverted orientation housing a used extravascular system according to the present disclosure.

Referring now to FIG. 5, the exemplary packaging system 100 is illustrated in an inverted orientation such that the base member 102 is supported by one or more landing surfaces 114. In this inverted orientation, the base member 102 is illustrated as a receptacle wherein a used needle assembly 20 has been temporarily placed within the opening 116 of the base member 102 prior to disposal of the needle assembly 20 into a sharps container. As illustrated, the enlarged pocket segment 110 of the base member provides sufficient storage space to house the tethered needle clip 24 following use of the extravascular system 10. Additionally, the outer surface of the enlarged pocket segment 110 comprises wing portion 112, each of which provide additional lateral support to the inverted base member 102.

Additionally, the one or more landing surfaces 114 may be configured so as to increase the stability of the base member 102 before and after use of the extravascular system 10. For example, prior to use of the extravascular system 10, a technician or clinician may invert the packaging system 100 in preparation of removing the cover member 104. The dimension and angle of the one or more landing surfaces 114 may be configured to optimize the angle of presentation to the technician as well as increase the stability of the packaging 100 to aid the technician in removing the cover member 104 as well as provide easy access to the extravascular system 10 once the cover member 104 has been removed.

Finally, as illustrated the wing portions 112 are configured to be in the same plane as the other landing surfaces 114 whereby the wing portions 112 and the other landing surfaces 114 all contribute to the overall stability of the base member 102 in an inverted orientation. Additional support features, such as feet, flares, or flange member may also extending laterally from base member 102 in the same plane as the wing portions 112 and the other landing surfaces 114 thereby further increasing the stability of the base member 102.

The present packaging systems provide a packaging system that meets the needs of extravascular system manufacturers and the needs of the extravascular system users. More specifically, the present packaging systems 100 provide a package that is compact for ease of storage and distribution and that promotes the sterility of the extravascular system. Additionally, the present packaging systems 100 provide a package that is easily opened by the user and that provides a more stable and sanitary package during the auxiliary uses developed by the medical practitioners. Accordingly, the present packaging systems are adapted to be simple product packaging and also adapted to serve as a functional tool during medical procedures.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the description recites "a" or "a first" element or the equivalent thereof, such description should be understood to include incorporation of one or more such elements, neither requiring nor excluding two or more such elements.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A packaging system for a catheter assembly comprising:
a base member including an elongate pocket adapted to receive a catheter assembly wherein the elongate pocket further comprises wing portions comprising the outer surface of the elongate pocket, the wing portions thereby providing lateral stability to the base member when inverted, the elongated pocket being shaped to approximate an outer profile of a catheter assembly;
a cover member adapted to selectively seal an opening of the base member;
wherein the base member comprises at least one landing surface upon which the base member may be inverted for use as a receptacle, wherein the at least one landing surface is sloped to maximize the contact between the at least one landing surface and a surface upon which the inverted base member is rested, the elongate pocket of the base member including an enlarged pocket segment adapted to accommodate the catheter assembly as configured prior to use and as configured following use when a needle cap of the catheter assembly is disposed around a needle tip of the catheter assembly.

2. The packaging system of claim 1, wherein the base member and the cover member are sealed together providing a blister package, the blister package further comprising a plurality of access points to facilitate removal of the cover member.

3. The packaging system of claim 2, wherein the plurality of access points are positioned at both a first end and a second end of the blister package.

4. The packaging system of claim 1, wherein the elongate pocket comprises an inner surface and an outer surface, the inner surface approximating an outer profile of the catheter assembly such that the catheter assembly is compatibly housed within the elongate pocket both prior to and following use of the catheter assembly, the outer surface thereby providing protection to the housed catheter assembly and providing lateral stability to the base member when inverted.

5. The packaging system of claim 1, wherein the at least one landing surface is sloped to provide a uniform plane along an outer surface of the base member to maximize contact between the at least one landing surface and the surface upon which the inverted base member is rested.

6. The packaging system of claim 1, wherein the at least one landing surface is sloped to provide a desired angle of presentation to a user when the base member is inverted.

7. The packaging system of claim 1, wherein the angle relative to the surface of the opening is selected to maximize the contact between the at least one landing surface and a surface upon which the inverted base member is rested.

8. The packaging system of claim 1, wherein the at least one landing surface includes two landing surfaces, and the two landing surfaces are coplanar.

9. A packaging system for an extravascular system comprising:
  a base member including an elongate pocket adapted to receive an extravascular system wherein the elongate pocket further comprises wing portions comprising the outer surface of the elongate pocket, the wing portions thereby providing lateral stability to the base member when inverted;
  a cover member selectively sealed to an opening of the base member and forming a blister package;
  a first access point disposed on a first end region of the blister package;
  a second access point disposed on a second end region of the blister package, the first and second end regions being on opposing portions of the blister package, the first and second access points being configured to facilitate removal of the cover member from the base member;
  wherein the base member comprises at least one landing surface upon which the base member may be inverted for use as a receptacle, the elongate pocket of the base member including an enlarged pocket segment adapted to accommodate the extravascular system as configured prior to use and as configured following use.

10. A packaging system for an extravascular system comprising:
  a base member including an elongate pocket, having an enlarged pocket segment at least one landing surface, and an opening wherein the elongate pocket further comprises wing portions comprising the outer surface of the elongate pocket, the wing portions thereby providing lateral stability to the base member when inverted;
  the enlarged pocket segment being adapted to accommodate an extravascular system as configured prior to use and as configured following use
  the at least one landing surface being the surface upon which the base member may be inverted for use as a receptacle, the landing surface being oriented on an angle relative to the surface of the opening of the base member; and
  a cover member adapted to selectively seal the opening of the base member.

* * * * *